United States Patent [19]

Dobert et al.

[11] Patent Number: 4,788,699
[45] Date of Patent: Nov. 29, 1988

[54] DENTAL X-RAY DIAGNOSTICS INSTALLATION FOR PRODUCING PANORAMA TOMOGRAMS OF THE JAW OF A PATIENT

[75] Inventors: Michael Dobert, Lorsch; Werner Gunther; Erich Heubeck, both of Bensheim, all of Fed. Rep. of Germany

[73] Assignee: Siemens Aktiengesellschaft, Berlin and Munich, Fed. Rep. of Germany

[21] Appl. No.: 17,544

[22] Filed: Feb. 24, 1987

[30] Foreign Application Priority Data

Feb. 28, 1986 [DE] Fed. Rep. of Germany ....... 3606654

[51] Int. Cl.⁴ .............................. G21K 1/04
[52] U.S. Cl. .................... 378/38; 378/147; 378/148; 378/149; 378/150
[58] Field of Search ............... 378/38, 147, 148, 149, 378/150

[56] References Cited

U.S. PATENT DOCUMENTS

| 581,199 | 4/1897 | Easton | 378/148 |
|---|---|---|---|
| 831,103 | 9/1906 | Ripperger | 378/148 |
| 3,631,249 | 12/1971 | Friede et al. | 378/148 |
| 4,048,498 | 9/1977 | Gerlach et al. | 378/148 |
| 4,166,220 | 8/1979 | Stutts | 378/148 |
| 4,195,229 | 3/1980 | Suzuki . | |
| 4,221,971 | 9/1980 | Burger . | |
| 4,679,221 | 7/1987 | O'Brien et al. | 378/148 |

FOREIGN PATENT DOCUMENTS 2949946 6/1981 Fed. Rep. of Germany .
2429584 1/1980 France .

OTHER PUBLICATIONS

Siemens sale brochure "Orthopantomograph 10," 1984.

Primary Examiner—Carolyn E. Fields
Assistant Examiner—David P. Porta
Attorney, Agent, or Firm—Hill, Van Santen, Steadman & Simpson

[57] ABSTRACT

A dental X-ray diagnostic installation for producing panoramic tomograms of the jaw of a patient is provided with a multiple diaphragm part having a plurality of different diaphragm apertures which can be adjusted to be positioned into a beam path from the X-ray source to enable producing different exposures. Preferably, the multiple diaphragm part is mounted for rotation on an axis so that the diaphragm apertures can be respectively aligned to the beam path of the radiation source. The multiple diaphragm part can be either a one-piece diaphragm member having a cylindrical configuration, a multiple piece member having a disk configuration, or can be a box-shaped carrier carrying a plurality of diaphragm inserts.

20 Claims, 6 Drawing Sheets

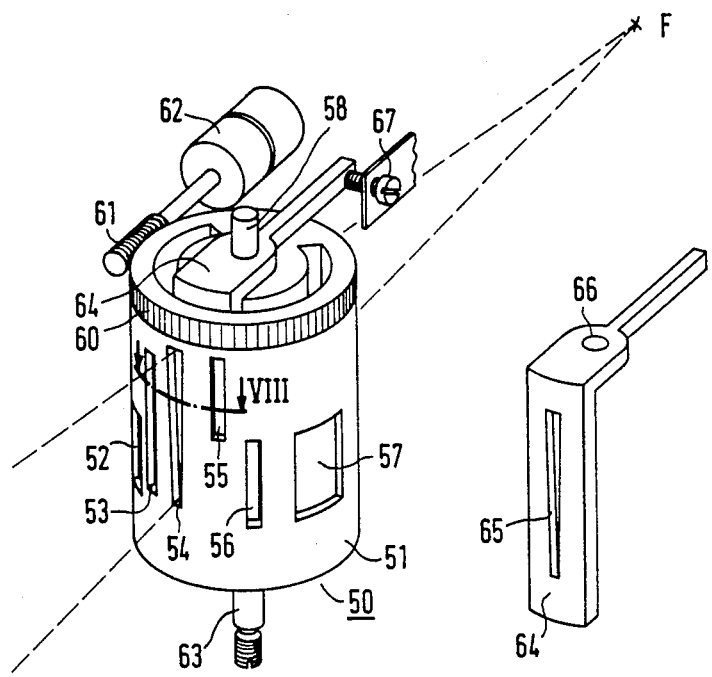
FIG 6
FIG 7
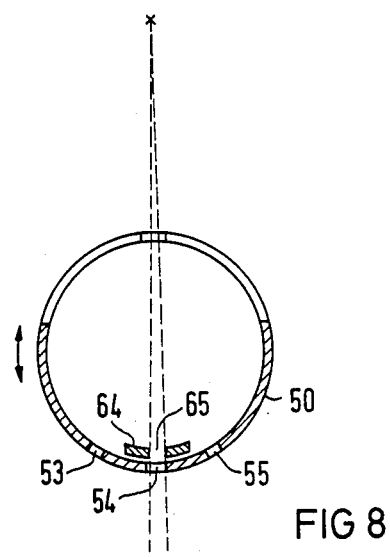
FIG 8

DENTAL X-RAY DIAGNOSTICS INSTALLATION FOR PRODUCING PANORAMA TOMOGRAMS OF THE JAW OF A PATIENT

BACKGRONND OF THE INVENTION

The invention is directed to a dental X-ray diagnostics installation for producing panorama tomograms of a jaw of a patient. The apparatus contains a radiation source or an x-radiator and a diaphragm arrangement which is positioned in a beam path between the radiator and the subject to be transilluminated.

In order to be able to produce different exposures, for example, exposures of the full upper jaw and lower jaw, exposures of only the upper jaw or only the lower jaw, exposures of a small jaw, such as of a child, or what are referred to as remote exposures with a known X-ray diagnostic installation or device, such as a ORTHOPANTOMOGRAPH 10, which is disclosed in a brochure entitled "ORTHOPANTOMOGRAPH 10, M/D 80/1361; WS 08832", it is necessary to replace the previously mounted diaphragm with another diaphragm having a different diaphragm aperture. Such an interchange is comparatively complicated and is relatively involved in some of the apparatuses which are commercially available because a number of parts therein must be dismantled and must, in turn, be rejoined or reconnected after the interchange and adjustment of the diaphragm insert.

SUMMARY OF THE INVENTION

The object of the present invention is to provide an improvement for an X-ray diagnostics installation so that different exposures can be produced without unnecessary delays for changing the diaphragm opening.

To accomplish these goals, the present invention is directed to an improvement in a dental X-ray diagnostics apparatus for producing panorama tomograms to the jaw of a patient, said X-ray diagnostics apparatus including a diaphragm for limiting the radiation beam which is positioned between the radiation source and a film cassette. The improvements are that a multiple diaphragm part, consisting of a plurality of different diaphragm apertures, is provided and the multiple diaphragm part is pivotably held so that it can be moved around an axis to present different diaphragm apertures in alignment to the beam path of the radiation source.

A multiple diaphragm part can be fashioned in the form of a one-piece diaphragm member having different diaphragm apertures or it can also be formed by individual diaphragm inserts provided with different diaphragm apertures which are held on a carrier, preferably in an interchangeable manner. The adjustment of the multiple diaphragm part, in order to bring the particular diaphragm or diaphragm aperture into the correct exposure position can occur manually or by utilizing a motor drive. In the case of a motor adjustment, it is advantageous to control the adjustment by a program. The particular advantages are achieved in combination with the modification of the speed of the film cassette because exposures can thus be made not only in different locations of the jaw, or respectively of the patients head, but can also be produced in different slice positions.

Other advantages, developments and improvements will be readily apparent from the following drawings, specification and claims.

BRIEF DESCRIPTION OF THE DRAWINGS

FIG. 6 is a perspective view of a second embodiment of a multiple diaphragm part of the present invention;

FIG. 7 is a perspective view of an auxilliary diaphragm part removed from the multiple diaphragm part of FIG. 6;

FIG. 8 is a cross-sectional view taken along the lines VIII—VIII of FIG. 6;

DESCRIPTION OF THE PREFERRED EMBODIMENTS

Figure 1:
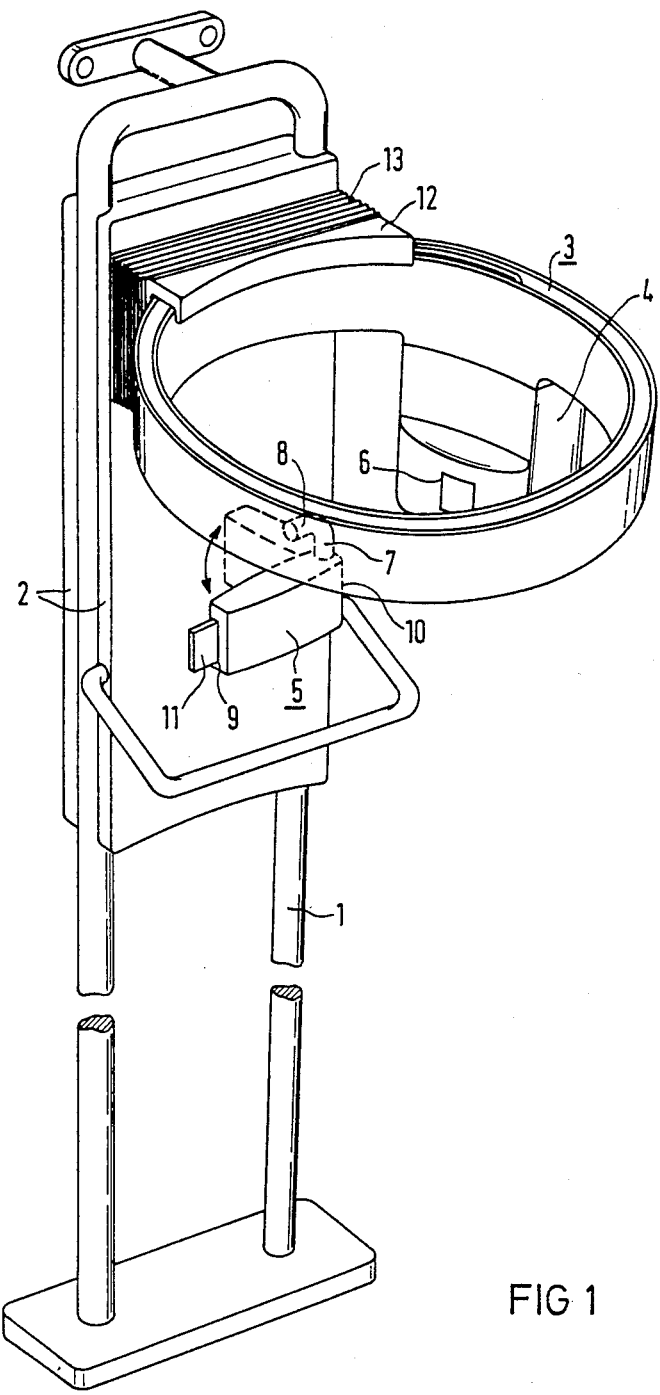
FIG. 1 is a perspective view of an X-ray diagnostics installation in accordance with the present invention.

The principals of the present invention are particularly useful in a dental X-ray diagnostics apparatus or installation schematically illustrated in FIG. 1. The X-ray installation or apparatus contains a stand 1 formed of two stand pipes on which a carriage 2 is held in a height-adjustable fashion. A rotary unit 3, which is illustrated as being in the form of a closed turntable ring, is held on the carriage 2 and this ring contains an X-ray radiator or source 4 and diametrically opposite a film cassette 5. The X-ray radiator 4, whose radiation exit window 6 faces the cassette, is mounted stationarily on the ring 3, which ring can be rotated as discussed hereinafter. The cassette 5 is pivotally mounted on a vertical axle 7 that has a portion 8 connected to the ring 3. The cassette 5 can be brought out of the position of use, shown with broken lines, into a non-use position, which is shown with solid lines, to allow an assistant to position the patient's head between the radiation source and the film cassette holder and to allww the production of remote exposures, which are referred to as Ceph exposures. In previous known apparatuses, the X-ray source had to be rotated to allow making such exposures.

The film cassette 5 contains a slot-like opening 9 on one end, and also an opening 10 on the opposite end so that a film cassette 11 can be introduced or, respectively, can be removed after the exposure. The film cassette, which is used, is a flexible film cassette provided with reinforcing foils as fundamentally employed for intra-oral exposures. The transport of the film cassette occurs by means of an electro-motive drive arranged in the film cassette holder 5.

The turntable ring 3 is held for rotation in a bearing part 12 and is also held so that it can be pivotted relative to the carriage 2. The adjustment mechanism (not shown in detal) required for this purpose is situated between the carriage 2 and the turntable ring 3 and is illustrated as being covered by an accordion bellows 13. On the basis of appropriate control of the adjustment mechanism, the adjustment mechanism allows the turntable ring and, thus, the position of the X-ray source 4 and the film cassette 5 to be brought into any arbitrary position required for rotation around the patient's head. In combination with the auto-rotation motion of the rotatable turntable ring 3 around its center axis and in combination with the film cassette adjustable in the cassette holder, the motion sequence of a desired exposure can thus be appropriately controlled.

Figure 2:
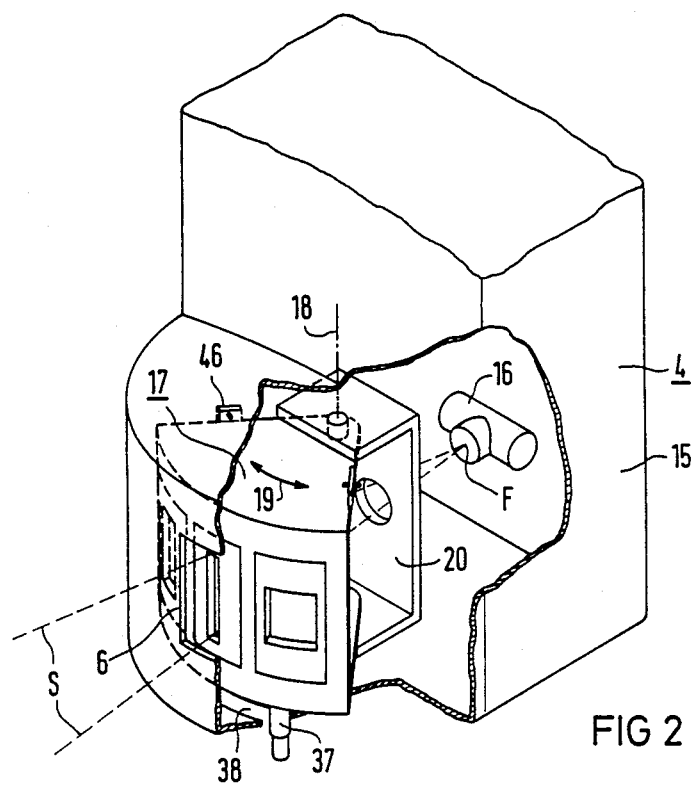
FIG. 2 is an enlarged perspective view with portions broken away for purposes of illustration of an X-ray source with a multiple diaphragm positioned in a beam path from the source.
Figure 3:
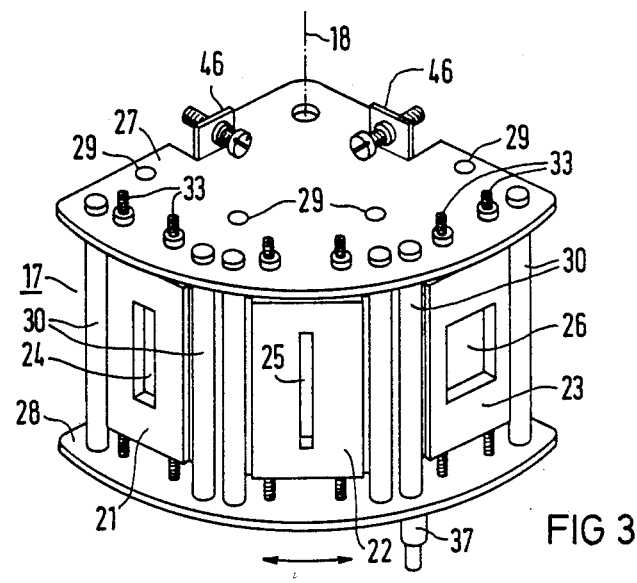
FIG. 3 is an enlarged perspective view of an embodiment of a multiple diaphragm part.

The X-ray radiator 4 is illustrated in greater detail in FIG. 2 and includes an X-ray tube 16, which is the axial X-ray source, and is arranged in a known way in the back part of a housing 15. The rays referenced R overall come from the X-ray tube 16 and the focus of the rays is referenced F. A multiple diaphragm part 17 is provided in the beam path between the X-ray source 16 and the window 6 of the housing 15. This multiple diaphragm part 17 is mounted for pivotal movement on a verticle axle or axis 18 in the housing 15 of the radiator 4 in a direction which is indicated by an arrow 19. A holding part 20, which is bent U-shaped and is provided with a corresponding opening for the passage of the radiation, is provided for mounting the multiple diaphragm part 17. As illustrated in FIG. 3, the multiple diaphragm part is composed of discrete parts. The multiple diaphragm part contains three diaphragm inserts 21, 22, and 23 with diaphragm apertures 24, 25 and 26, respectively, of different sizes. Two plates, 27 and 28, each of which has a shape of a circular segment of about 110°, are provided for the mounting of the diaphragm inserts 21-23, and these plates are held in spaced relationship by a plurality of perpendicular retaining pins 29. Expediently, the spacer pins 29 are clinch bolts which rigidly fix the two plates 27, 28 relative to one another to form a box-like structure.

Figure 4:
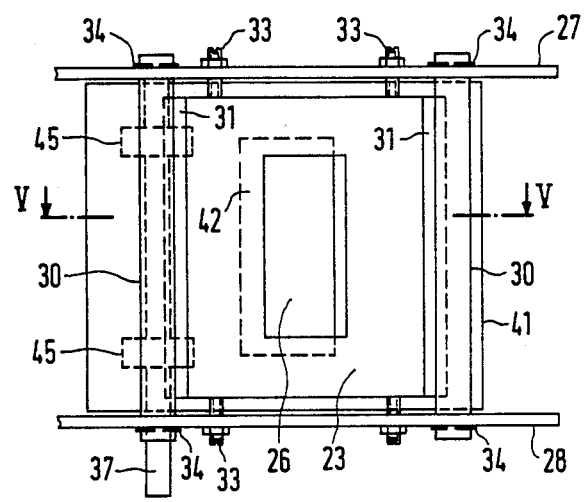
FIG. 4 is an end view of the multiple diaphragm part of FIG. 3.

Retaining pins 30 are provided in pairs in a peripheral region of the plates 27, 28 for mounting the diaphragm inserts 21-23. Additional details of these pins are shown in FIG. 4. For example, a diaphragm insert 23 contains guide noses or ridges 31 on both sides which noses are engaged in longitudinal slots 32 of the retaining pins 30. The guide nose 31 and slots 32 are constructed so that the diaphragm insert can be guided and held with little play.

Adjustment screws 33 are provided in the two plates 27, 28. The diaphragm inserts are, thus, capable of being aligned to the central ray or, respectively, to the axis of the beam path of the radiator 16 with the assistance of these adjustment screws 33.

The retention of the retaining bolts or pins 30 at the plates 27, 28 occurs by means of easily removable lock rings or snap rings 34, wherein the interchange of the diaphragm inserts can be undertaken in a very easy manner. For this purpose, it is essential to only remove one locking ring of one retaining pin. Then, the retaining pin can be pulled out in either an upward or downward direction, depending on which locking ring has been removed. Subsequently, the diaphragm insert can be removed, given a slight swivelling or pulling motion and rotation of the other retaining pin. The insertion of a new diaphragm insert with a different diaphragm aperture occurs by positioning the edge of the new diaphragm insert in the groove 32 of the pin 30, then inserting the previously removed pin with its groove receiving the edge noses on the opposite edge.

Figure 5:
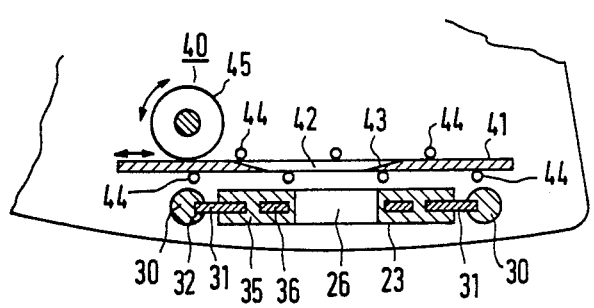
FIG. 5 is a cross-sectional view taken along the lines V—V of FIG. 4.

The structure of the diaphragm insert is best illustrated in FIG. 5, in which the diaphragm insert 23, which is specifically suited for what is called a Ceph exposure, for example a skull exposure, is illustrated.

The diaphragm insert is composed of a base member 35 of lead which contains the diaphragm aperture 26. A sheet metal carrier 36 forming the guide noses 31 is embedded in the edges of the member 35.

As already mentioned, the overall diaphragm arrangement 17 can be pivoted around the axle on the axis 18. To this end, a manually adjustment lever 37 (FIGS. 2, 3 and 4) is provided on the lower plate 28 and this adjustment lever projects downward through a corresponding provided slot 38 (FIG. 2) and, thus, is capable of being manually grasped. At the same time, the adjustment lever 37 is expediently the axle of the adjustment drive 40 (FIG. 5) for a soft tissue filter 41 which is additionally provided between the diaphragm arrangement 17 and the focus F. This soft tissue filter 41 is preferably composed of a copper plate having a window 42 which has bevelled edge surfaces 43 on at least both sides and, thus, comprises differing material thicknesses in this region so that a different soft-focus registration, which is specifically desired with a Ceph exposure, is achieved and dependeds upon how far the plate comprising the bevelled window surface is introduced into the beam path. In order to obtain a good guidance of the copper plate 41, small guidance elements 44 in the form of projections or the like are provided on the two plates 27, 28.

As shown, the adjustable drive can be formed by two friction wheels 45 which are secured to the axle 37. Instead of the friction wheels, a roller or some other suitable adjustment drive, for example a drive composed of a gear, can be employed. As set forth with reference to the following exemplary embodiments, the drive can also be an electro-motive drive which adjusts the multiple diaphragm part with the assistance of a control means dependent on the selection of the exposure to be provided until the desired diaphragm or, respectively, diaphragm aperture is located in the beam path of the radiator.

The adjustment path or swivel path of the multiple diaphragm part is limited by stop members 46 (see FIGS. 2 and 3), which are arranged at both sides of the upper plate 27. These limit stop elements 46 are adjustably constructed in order to be able to set the diaphragm arrangement precisely to the beam path. In order to obtain an unequivocal allocation and fixing of the individual diaphragms to the beam path, the middle portion in which the diaphragm opening lies exactly in the beam path can be defined by suitable catch means, for example by a ball catch or detent, which is not shown in the drawings.

Other embodiments of the multiple diaphragm are illustrated in FIGS. 6, 7, 8 and 10. In contrast to the multiple diaphragm 17 of FIGS. 2-5, a multiple diaphragm part 50 is shown schematically in FIG. 6 and is fashioned as a one-piece, hollow cylindrical diaphragm member on whose cylindrical generated surface 51 a radiation passage opening 52 as well as diaphragm apertures 53-57 which have different diaphragm widths and heights are provided. The diaphragm apertures 53-57 are suitable for the following exposures: Diaphragm aperture 53 for exposures of lower and upper jaw of children; Diaphragm aperture 54 for exposures of lower and upper jaw of adults utilizing a standard exposure; Diaphragm aperture 55 for exposures of only upper jaw; Diaphragm aperture 56 for exposures of only lower jaw; and Diaphragm aperture 57 for Ceph (skull) exposures. The aperture 52 is provided for the purpose of having a free radiation passage given a set diaphragm aperture 57.

The diaphragm member 50 is dynamically balanced and is pivotable or rotated around a rotational axis 58. The axis 58 corresponds to a swivel axis 18 around which the multiple diaphragm part 17 of FIG. 2 was rotated or pivoted. The adjustment of the diaphragm member 50 occurs utlizing an electromotive drive for which purpose teeth 60 are provided on a circumference of the member 50. A pinion or worm gear 61 of an electro-motive drive 62 engages the teeth 50. A stepping motor or some other suitable drive can be provided for the drive motor.

A set screw 63 is provided at a suitable location in order to enable the alignment of the multiple diaphragm part 50 to the beam path in a direction parallel to the axis 58.

In order to obtain an attenuated radiant intensity in the region of the front teeth, particularly given standard exposures, an auxilliary diaphragm 64, which is a lead diaphragm is provided in the beam path between the focus F and the openings in the member 50. This auxilliary diaphragm 64 is illustrated in greater detail in FIG. 7 and it contains a diaphragm aperture 65 corresponding to the aperture 54. The auxilliary diaphragm 64 is held in a pivotable fashion by having a bore or cylindrical bearing 66 received on the axle forming the axis 58. As fundamentally shown in FIG. 8, the diaphragm aperture 65 can, thus, be set somewhat offset relative to the diaphragm aperture 54 of the diaphragm member 50 so that an edge shift and, thus, a different radiant intensity on the film within the slot width will occur. The degree of the edge shift can be infinitely varied by means of a set screw 67.

A further crucial advantage of the multiple diaphragm part provided in accordance with the invention is that a matching to nationally specified formats or sizes having different units of measure (for example inches) can be achieved in a relatively simple way. While retaining the rest of the structure, either the individual diaphragm insert or the entire diaphragm member can be replaced.

Figure 9:
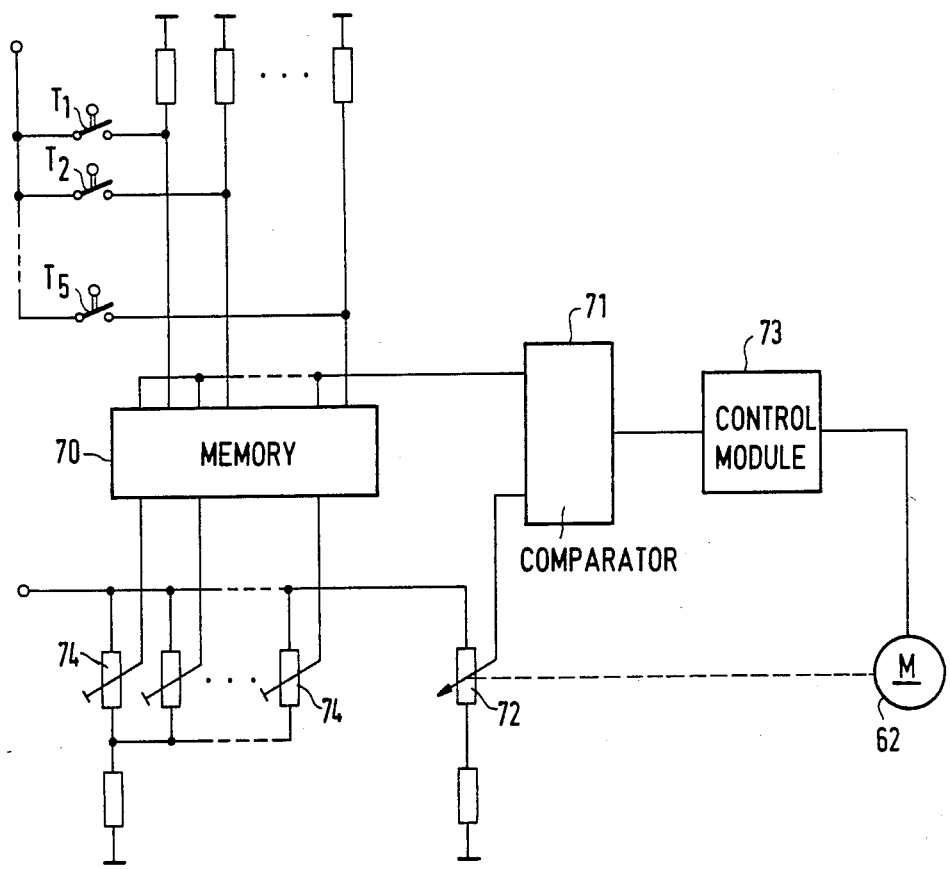
FIG. 9 is a fundamental circuit diagram for control of the movement of the multiple diaphragm part.

In FIG. 9, a fundamental circuit diagram for controlling the drive motor 62 is illustrated. It is assumed that every diaphragm position is determined by a defined x-rated value which is deposited in a suitable memory 70, for example a read-only memory. The stored values can be called in by keys T1-T6, which correspond to the selectable diaphragm apertures 52-57. The stored values, when called from the memory, are supplied to a rated /actual comparator 51 to which the respective axial position of the motor 62 and, thus, of the diaphragm member 50, is supplied through an actual value generator 72. A control module 73 receives the output from the comparator 71 and drives the motor 62 until the rated and actual values coincide, for example, until the diaphragm or, respectively, diaphragm opening which has been called or selected, is situated in the intended exposure position. A variety of adjustment potentiometers 74 are also provided for the precise adjustment of a diaphragm position.

Figure 10:
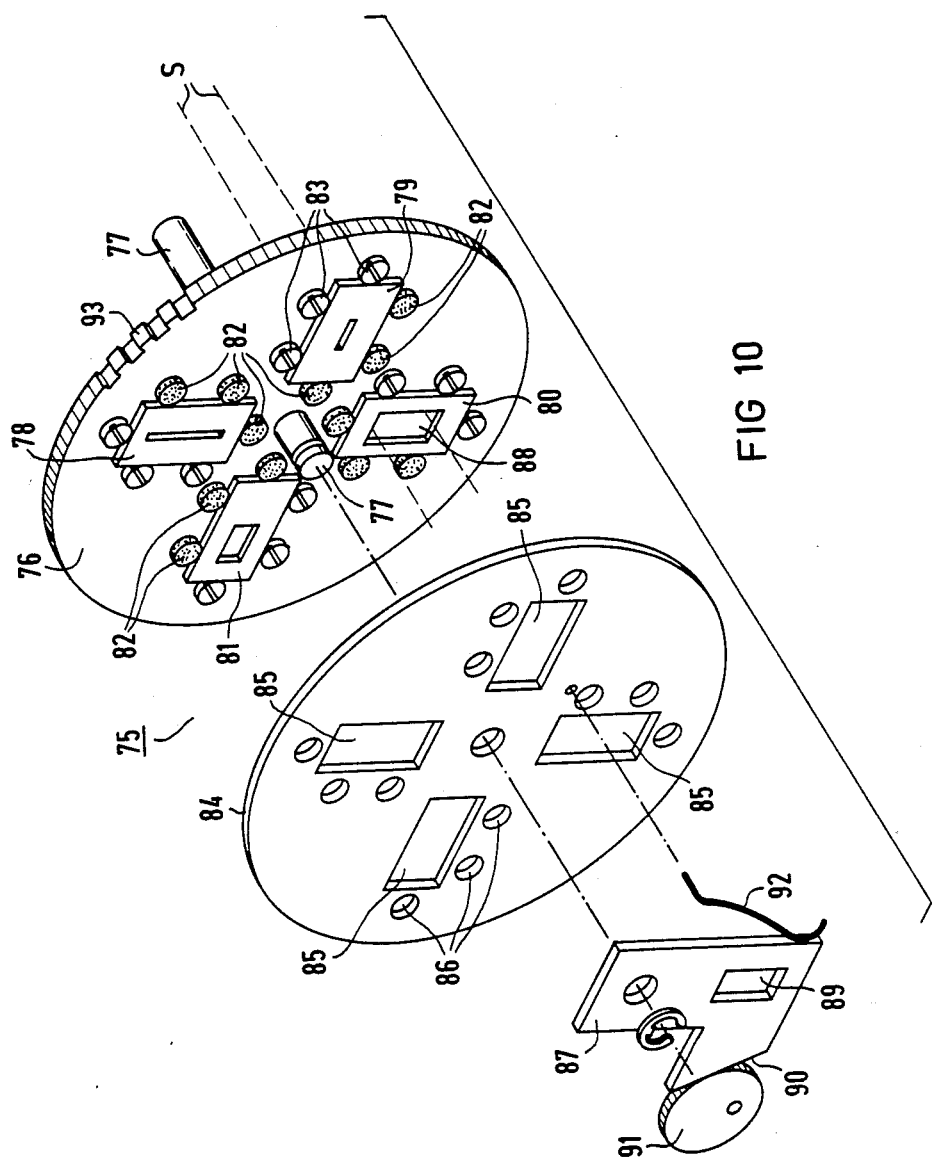
FIG. 10 is an exploded perspective view of another embodiment of a multiple diaphragm part in accordance with the present invention.

Another embodiment of a multiple diaphragm part is shown in an exploded view in FIG. 10, and is overall identified by element 75. The part 75 contains a disk-shaped carrier part 76, which is rotatably mounted in the housing of the x-radiator 4 on a shaft 77. A retaining part equivalent to the retaining part 20 in FIG. 2 can be provided for this purpose. The carrier part 76 is mounted such that the diaphragm apertures of four diaphragm inserts 78-81 are arranged on the part 76 in a plane lying perpendicular to the rotational axis and are aligned to the beam path S of the x-radiator 16 when the part 76 is rotated on the shaft 77. The diaphragm inserts 78-81 are adjustably arranged for precise adjustment of their apertures by mounting means. In the present exemplary embodiment, the mounting means includes resilient elements in the form of members 82 of cellular material which lie at two neighboring or adjacent side edges of the diaphragm inserts and eccentrically seated set screws 83 are provided on the remaining other two side edges. Diaphragm inserts, resilient elements and eccentric set screws are expediently inserted into the corresponding depressions (not shown here) of a carrier part 76 so that their outside edges can terminate flush with the end face of the carrier part 76. A cover plate 84, which is likewise disk-shaped, lies against this end face in the assembled condition and this cover plate is connected to the carrier part 76 by means of fastening elements (not shown). The cover plate 84 has rectangular openings 85 of identical size, which at least correspond to the largest diaphragm aperture of the diaphragm insert 78-81. Additional bores 86 corresponding in size and shape to the eccentric set screws are provided so that a tool for adjustment of the eccentric set screws 83 can be introduced through the bores 86 after the two parts 76 and 84 have been secured together.

Finally, a soft tissue filter 87 corresponding to the soft tissue filter 41 in FIGS. 4 and 5 is also put in place on the shaft 77. This soft tissue filter 87 comprises an opening 89 corresponding to a diaphragm aperture of a diaphragm insert, for example the aperture 88 of the diaphragm 80. Like the soft tissue filter 41, the soft tissue filter 84 is composed of a material, for example copper, with which a different soft tissue or soft focus registration of the subject can be achieved, for example, given skull exposures. Bevelled window surfaces are also provided here in order to achieve a soft transition. The soft tissue filter 87 contains an angular extending surface 90 against which an eccentrically seated adjustment wheel or cam 91 presses. The soft tissue filter 87 is then capable of being pivoted into the beam path of the x-radiator to a greater or lesser degree with the turning of the cam or wheel 91 which will thus shift the aperture 89 from overlying the aperture 88 to being offset thereto. A resilient member or leaf spring 92 is mounted on the plate 84 to hold the surface 90 against the wheel 91.

Both the adjustment wheel 91, as well as the carrier part 76, can be adjusted either manually or by a motor. An appropriate profile, which is referenced 93, for the carrier part 76 is expediently provided on the circumference to be engaged by a drive means. For example, this profile can cooperate with a belt having a corresponding tooth profile.

The diaphragm inserts 78-81 are identical in terms of outside dimension so that they can be easily interchanged for one another respectively, so that a sequence of their arrangement on the carrier part 76 can be randomly selected. Accordingly, the openings 85 in the cover plate and the openings in the carrer part 76 are also of equal size.

Of course, the resilient elements fashioned in some other way can also be provided instead of the disk-shaped laminae of cellular material which are shown.

Although various minor modifications may be suggested by those versed in the art, it should be understood that we wish to embody within the scope of the patent granted hereon all such modifications as reasonably and properly come within the scope of our contribution to the art.

We claim:

1. In a dental X-ray diagnostics apparatus for producing panoramic tomograms of a jaw of a patient, said apparatus including a radiation source creating a beam of radiation directed in a beam path towards a film cassette, and a diaphragm being positioned in the beam path of the radiation beam for limiting the size of said beam the improvements comprising said diaphragm being a multiple diaphragm part having a plurality of diaphragm inserts with different diaphragm apertures, said part being mounted for rotation around an axis to position different diaphragm apertures in the beam path from the radiation source and means for adjustably mounting the inserts on the diaphragm part, said means for adjustably mounting including adjustment elements enabling selectively positioning each insert relative to the beam path when the insert is positioned in said beam path.

2. In a dental X-ray diagnostics apparatus according to claim 1, wherein the multiple diaphragm part contains a diaphragm member which is symmertrical to said axis and has an axle bearing being mounted to rotate around an axle on said axis.

3. In a dental X-ray diagnostics apparatus according to claim 2, wherein said diaphragm member is provided with teeth on a circumferential portion of the diaphragm member for engagement by a drive motor to rotate said member.

4. In a dental X-ray diagnostics apparatus according to claim 2, which further includes an auxilliary diaphragm being pivotally mounted on the axle bearing of the diaphragm member, said auxiliary diaphragm having a diaphragm aperture being movable relative to the selected diaphragm aperture so that its adjustment relative to the selected diaphragm aperture of the diaphragm member enables varying the effective diaphragm width of the diaphragm aperture of the diaphragm member.

5. In a dental X-ray diagnostics apparatus according to claim 4, wherein the range of adjustment of said auxilliary diaphragm is obtained by a variable stop means.

6. In a dental X-ray diagnostics apparatus according to claim 1, wherein the multiple diaphragm part contains a carrier part mounted for pivotal movement through an arc around a rotation axis, said carrier part receiving said plurality of diaphragm inserts each containing a different diaphragm aperture, said diaphragm inserts being interchangeably mounted on said carrier part.

7. In a dental X-ray diagnostics apparatus according to claim 6, wherein said carrier part is formed by two parallel extending plates, each having a shape of a sector of a circle, said plates being held apart by spacing members and retaining pins, said retaining pins having longitudinally extending slots arranged therein, the individual diaphragm inserts having edge portions received in said slots of the retaining pins to mount the insert on the carrier, said retaining pins being secured in the plates by means of easily releasable fastening elements so that removing one retaining pin of a pair enables replacing the diaphragm insert held therebetween.

8. In a dental X-ray diagnostics apparatus according to claim 6, wherein each of the diaphragm inserts is composed of a base member of lead containing a diaphragm aperture and of a sheet of carrier material inserted therein and forming guide elements for being used in interchangeably mounting the insert on said carrier part.

9. In a dental X-ray diagnostics apparatus according to claim 1, wherein the multiple diaphragm part comprises a disk-shaped carrier part having said means for adjustably mounting the diaphragm inserts, said disk-shaped part being mounted for rotation on an axle with the plane of the disk-shaped part and inserts extending perpendicular to the beam path, and said diaphragm apertures of each of the diaphragm inserts being indexed into the beam path of the radiation source by rotating said carrier part on said axle.

10. In a dental X-ray diagnostics apparatus according to claim 9, wherein the means for adjustably mounting the diaphragm inserts on the disk-shaped carrier part includes resilient elements engaging two adjacent edges of each diaphragm part and the adjustable elements engaging the other two edges, a disk-shaped cover plate covering the diaphragm inserts and being secured to said carrier part, said cover plate having openings enabling access to the adjustment elements of the carrier part.

11. In a dental X-ray diagnostics apparatus according to claim 9, wherein each of the diaphragm inserts is identical in structural size.

12. In a dental X-ray diagnostics apparatus according to claim 9, which includes a soft tissue filter having a filter aperture, said soft tissue filter being mounted on said axle, and said apparatus including means for positioning the filter aperture relative to a diaphragm aperture and for changing the position of the soft tissue filter relative to the beam path.

13. In a dental X-ray diagnostics apparatus according to claim 1, wherein at least one of the diaphragms is provided with a soft tissue filter, means for adjusting the position of said soft tissue filter relative to the diaphragm aperture of said multiple diaphragm part.

14. In a dental X-ray diagnostics apparatus according to claim 13, wherein the means for adjusting includes friction drive means engaging said filter for moving said filter along a path relative to the diaphragm aperture of said diaphragm.

15. In a dental X-ray diagnostics apparatus according to claim 14, wherein the friction drive means has a shaft extending through the housing for the multiple diaphragm part, said shaft being an adjustment shaft for rotating the diaphragm part to present different diaphragm apertures in the beam path.

16. In a dental X-ray diagnostics apparatus according to claim 1, wherein the axis of rotation for the multiple diaphragm part extends close to the focal point of the radiation source.

17. In a dental X-ray diagnostics apparatus for producing panoramic tomograms of a jaw of a patient, said apparatus including a radiation source creating a beam of radiation directed in a beam path towards a film cassette, and a diaphragm being positioned in the beam path of the raidation beam for limiting the size of said beam the improvements comprising said diaphragm being a multiple diaphragm part, said diaphragm part being a cylindrical member having a cylindrical surface with a plurality of different diaphragm apertures being formed in said cylindrical surface, said cylindrical member being mounted for rotation around an axis to position different diaphragm apertures in the beam path from the radiation source.

18. In a dental X-ray diagnostics apparatus according to claim 17, wherein said cylindrical member is provided with teeth on a cylindrical surface of the member for engagement by a drive motor to rotate said member.

19. In a dental X-ray diagnostics apparatus according to claim 17, whrein the cylindrical member has an axle bearing mounted to rotate around an axle on said axis of rotation, and said apparatus includes an auxilliary diaphragm being pivotally mounted on the axle bearing of the cylindrical member, said auxilliary diaphragm having a diaphragm aperture being movable relative to the selected diaphragm aperture so that its adjustment relative to the selected diaphragm aperture of the member enables varying the effective diaphragm width of the diaphragm aperture of the member.

20. In a dental X-ray diagnositcs apparatus according to claim 19, wherein a range of adjustment of said auxilliary diaphragm is obtained by a variable stop means.

* * * * *